United States Patent [19]

Diamond et al.

[11] Patent Number: 6,056,923
[45] Date of Patent: May 2, 2000

[54] DUAL INJECTOR FOR CHEMILUMINESCENCE IMMUNOANALYZING SYSTEM

[75] Inventors: Ronald N Diamond, Anaheim Hills; Michael Otter, Dana Point; Thomas Sheng-Shyong Hu, Rancho Santa Margarita; William A Stark, Costa Mesa, all of Calif.

[73] Assignee: CLMP, Inc., Wilmington, Del.

[21] Appl. No.: 08/882,414

[22] Filed: Jun. 25, 1997

[51] Int. Cl.⁷ .................................................... G01N 35/10
[52] U.S. Cl. .............................. 422/100; 422/81; 436/54; 436/180
[58] Field of Search ................................ 422/63, 68.1, 52, 422/81, 100, 103; 436/43, 49, 54, 174, 160, 183

[56] References Cited

U.S. PATENT DOCUMENTS

| | | | |
|---|---|---|---|
| 4,018,883 | 4/1977 | Parslow . | |
| 4,104,126 | 8/1978 | Young . | |
| 4,277,249 | 7/1981 | Broughton . | |
| 4,681,742 | 7/1987 | Johnson et al. | 422/102 |
| 4,687,747 | 8/1987 | Lin . | |
| 4,803,050 | 2/1989 | Mack | 422/65 |
| 4,861,554 | 8/1989 | Sakuma | 422/65 |
| 4,935,339 | 6/1990 | Zahradnik . | |
| 4,963,256 | 10/1990 | Nelson . | |
| 5,089,424 | 2/1992 | Khalil et al. | 436/518 |
| 5,139,745 | 8/1992 | Barr et al. | 422/82.05 |
| 5,244,630 | 9/1993 | Khalil et al. | 422/52 |
| 5,395,938 | 3/1995 | Ramakrishnan . | |
| 5,439,649 | 8/1995 | Tseung et al. | 422/99 |
| 5,632,399 | 5/1997 | Palmieri et al. . | |
| 5,650,122 | 7/1997 | Harris et al. | 422/81 |

OTHER PUBLICATIONS

The Application of Chemiluminescence in Diagnostics; McCapra; transcript of lecture . . . American Association of Clinical Chemists—New Orleans, LA, Jul. 28, 1988.

*Primary Examiner*—Long V. Le
*Attorney, Agent, or Firm*—Stout, Uxa, Buyan & Mullins, LLP; Donald E. Stout

[57] ABSTRACT

A dual injector for an automated immunoassay instrument is provided which allows the sequential detection of two different chemiluminescence labels within one instrument. The injector has four carefully designed orifices. The orifices are designed to work in two pairs. Orifices one and two can be used to inject trigger reagents A and B which can trigger a chemiluminescent reaction, such as acridinium. Orifices three and four can inject trigger reagents C and D for triggering a chemiluminescent reaction, such as luminol. The two pairs can be used in a sequential manner to generate signals in the wells of a cuvette. Thus, it is possible to run both acridinium and luminol based assays on one instrument.

22 Claims, 7 Drawing Sheets

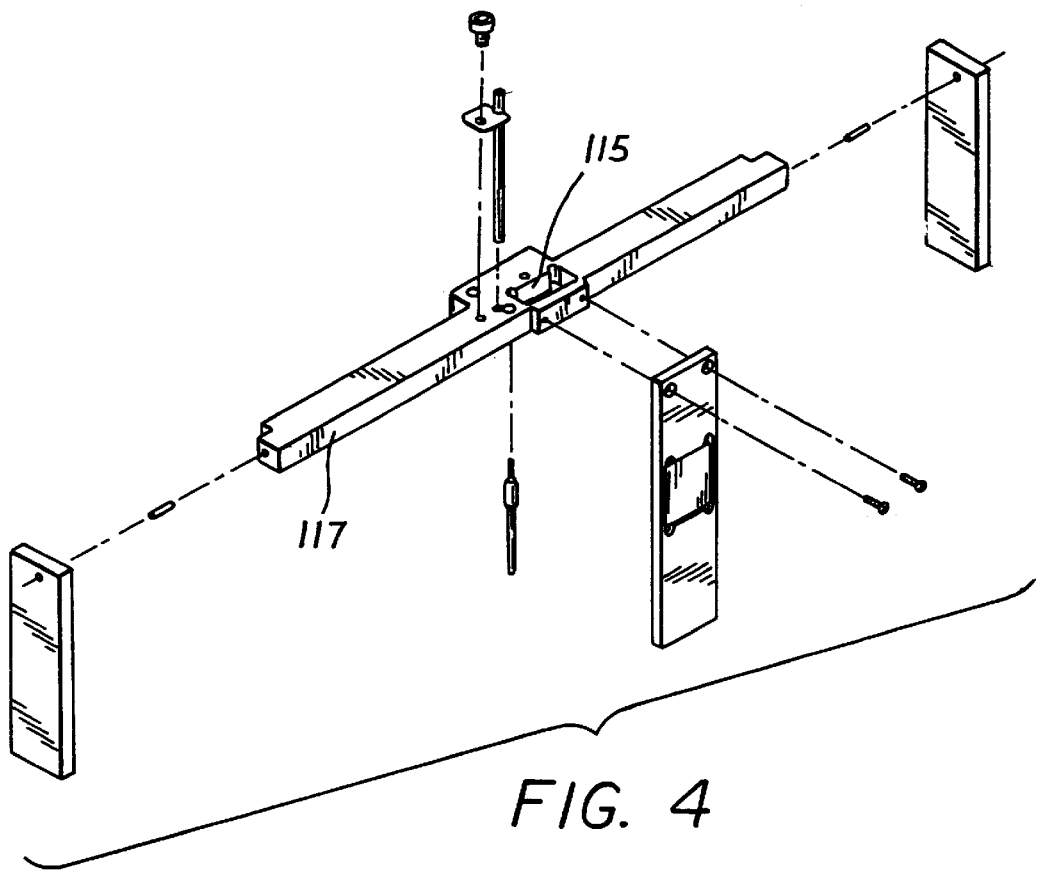
FIG. 4
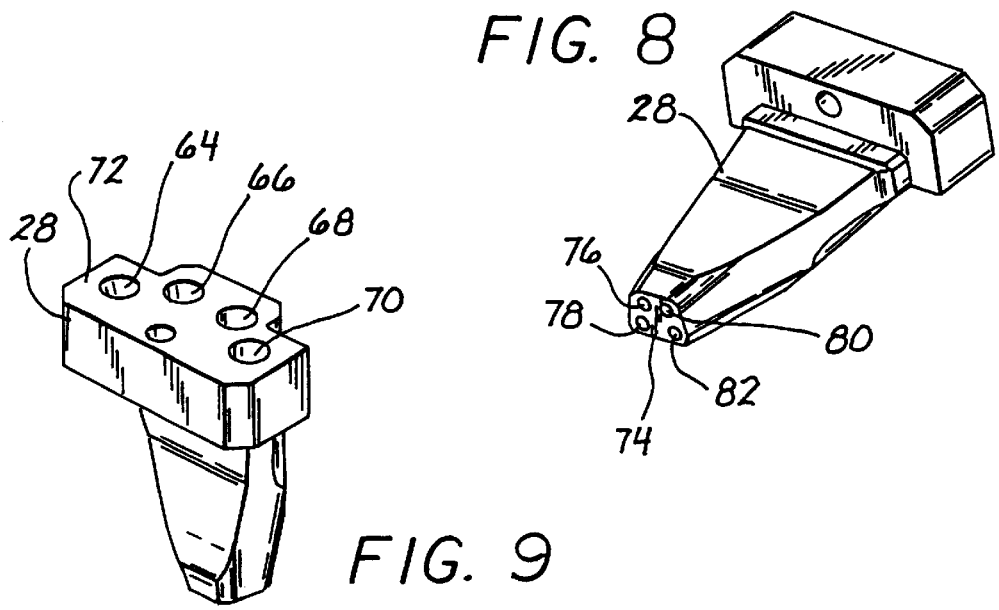
FIG. 8
FIG. 9

DUAL INJECTOR FOR CHEMILUMINESCENCE IMMUNOANALYZING SYSTEM

FIELD OF THE INVENTION

The present invention relates to the field of immunoassay procedures, and more particularly to a dual injector design for use with compounds which enable detection of immunological substances or other analytes through chemiluminescence.

BACKGROUND OF THE INVENTION

Immunoassay is an analytical technique widely used in medicine and in the biological sciences. The term "immunoassay" as used herein encompasses analytical methods for detecting, locating or quantifying biological substances by use of a label. Generally, a "label" is attached to a molecule of the substance of interest. The presence of the labeled molecule can then be detected by suitable means.

There are various types of immunoassay in common usage. In one type of immunoassay, a sample containing both an unknown and a labeled antigen of interest is incubated with an antibody specific for that antigen. If the unknown also contains the antigen, then both the labeled and unlabeled antigens compete for binding sites on the antibody. The antibody can be immobilized on a solid support, such as a test tube, glass beads, latex particles, or the like. Incubation is followed by a separation step in which the antigen bound to the antibody on the support is separated from unbound antigen. Through measurement of the amount of bound labeled antigen, the presence and/or quantity of similar, unlabeled antigen can be determined. Thus, the detected level of the labeled antigen (e.g. counts per minute of radioactivity) is an inverse function of the concentration of the unlabeled antigen.

A second type of immunoassay is known as sandwich immunoassay. In this method, an antibody rather than an antigen is labeled. A sample containing an unknown is incubated with an immobilized antibody. Antigens, if present in the sample, will bind to the antibody. After incubation, unbound material is removed by a separation step. In a second incubation with a solution of labeled antibody, the bound antigen is "sandwiched" between the immobilized antibody and the labeled antibody which adheres to the antigen. After a second separation, the amount of labeled antibody is determined. Detection of labeled antibody is indicative of the presence of antigen.

In general, a commonly used type of label is a radioactive substance, which can easily and accurately be detected. However materials labeled radioactively often have a short shelf life, both because of radioactive decay of the label and because radiation degrades the labeled molecule. Further, handling of radioactive substances entails risks to laboratory personnel.

In contrast to radioimmunoassay, luminometric immunoassay utilizes a chemiluminescent compound as the label. Such a compound is capable of undergoing a reaction (usually oxidative) in which light is a product. The light emission is measured by appropriate devices, and in certain cases, the light intensity is indicative of the quantity of labeled material. Known chemiluminescent substances suitable for use as immunoassays include luminol, isoluminol, and the various acridinium esters, for example, as noted in the prior art literature, and discussed in U.S. Pat. No. 5,395,938, to Ramakrishnan, which is commonly assigned with the present application.

Luminometric immunoassay procedures overcome many of the problems encountered with radioimmunoassay, namely risk to personnel and the short shelf life due to radioactive decay. Additionally, for example, luminometric immunoassay is easier to use, requires a shorter incubation time, solves problems related to safety, waste disposal, and regulatory compliance, has greater sensitivity, utilizes more stable reagents, and improves ease of manufacture and storage.

It is known in the prior art to employ an automated chemiluminescence immunoassay analyzer for assaying specimens. Such automated systems typically employ a set of two trigger reagents A and B which can trigger a chemiluminescent reaction, in labels such as either luminol or acridinium. The trigger reagents are sequentially injected into a receptacle, such as the well of a cuvette, when the cuvette is disposed in the measuring chamber of the analyzer. When the chemiluminescent reaction is initiated by the injection of the trigger reagents, the flash resulting from the oxidation of the label to its excited state, and its subsequent return to the ground state, which typically lasts about two seconds, is detected by the system integrated luminometer. This value is expressed in relative light units (RLU), and compared to a calibrated test standard in order to determine the amount of bound labeled antibody or antigen in the patient's blood.

Assays are available to test a variety of body functions, including, for example, the adrenal/pituitary system, anemia, bone and mineral metabolism, growth, thyroid, tumor markers, hypertension, neonatal conditions, and the reproductive system. It would be advantageous to be able to perform a plurality of such assays, of different types, on a single immunoassay instrument, in a single procedure, using a plurality of labels, and a plurality of triggering reagent sets to initiate a chemiluminescent reaction for each of the labels sequentially. It would further be advantageous to be able to inject the triggering reagents of each set in such a manner that the walls of the cuvette well are washed down and cross-contamination between trigger reagents exiting each of the exit ports of the trigger reagent injector is substantially eliminated.

SUMMARY OF THE INVENTION

A dual injector for an automated immunoassay instrument is provided which allows the sequential detection of two different chemiluminescence labels within one instrument. The injector has four carefully designed orifices. The orifices are designed to work in two pairs. Orifices one and two can be used to inject trigger reagents A and B which can trigger a chemiluminescent reaction, such as acridinium. Orifices three and four can inject trigger reagents C and D for triggering a chemiluminescent reaction, such as luminol. The two pairs can be used in a sequential manner to generate signals in the wells of a cuvette. Thus, it is possible to run a plurality of assays, such as both acridinium and luminol based assays, for example, on one instrument.

The injector is designed to fit into the wells of the cuvette and to inject the triggers in a manner which efficiently resuspends magnetic particles of one to eight microns in diameter. The design also prevents the contamination or carryover of trigger solutions from one orifice to another.

More particularly, in one aspect of the invention, a dual injector system for an automated chemiluminescent immunoassay instrument is provided which comprises a first pair of injector orifices for injecting first and second trigger reagents into a well containing a chemiluminescent label and a second pair of injector orifices for injecting third and fourth trigger reagents into a well containing a chemiluminescent label. This advantageous arrangement permits the running of a plurality of assays in a single instrument.

In another aspect of the invention, an injector system for an automated chemiluminescent immunoassay instrument is provided which comprises an injector body having a longitudinal axis, a first injector orifice disposed in the injector body for injecting a first trigger reagent into a well containing a chemiluminescent label; and a second injector orifice disposed in the injector body for injecting a second trigger reagent into a well containing a chemiluminescent label. Advantageously, the first injector orifice is disposed at a compound angle with respect to the longitudinal axis, such that the first orifice is disposed at an angle to the as in a plurality of planes, preferably two. This allows the orifice to inject the first trigger reagent at an angle into the cuvette well, so that it washes the magnetic particles into the assay solution. It also allows the employment of four injector orifices for injecting more than one set of trigger reagents in a single immunoassay instrument, without contaminating cross-talk between sets of orifices.

The invention, together with additional features and advantages thereof, may best be understood by reference to the following description taken in conjunction with the accompanying illustrative drawing.

BRIEF DESCRIPTION OF THE DRAWING

FIG. 4 is a perspective view, in an exploded format, of a beam for supporting a trigger injector constructed in accordance with the principles of the present invention;

FIG. 8 is a perspective view, in isolation, illustrating the top side and distal end of a trigger injector constructed in accordance with the principles of the present invention;

FIG. 9 is a perspective view, in isolation, illustrating the top side and proximal end of the trigger injector shown in FIG. 8;

DESCRIPTION OF THE INVENTION

Figure 1:
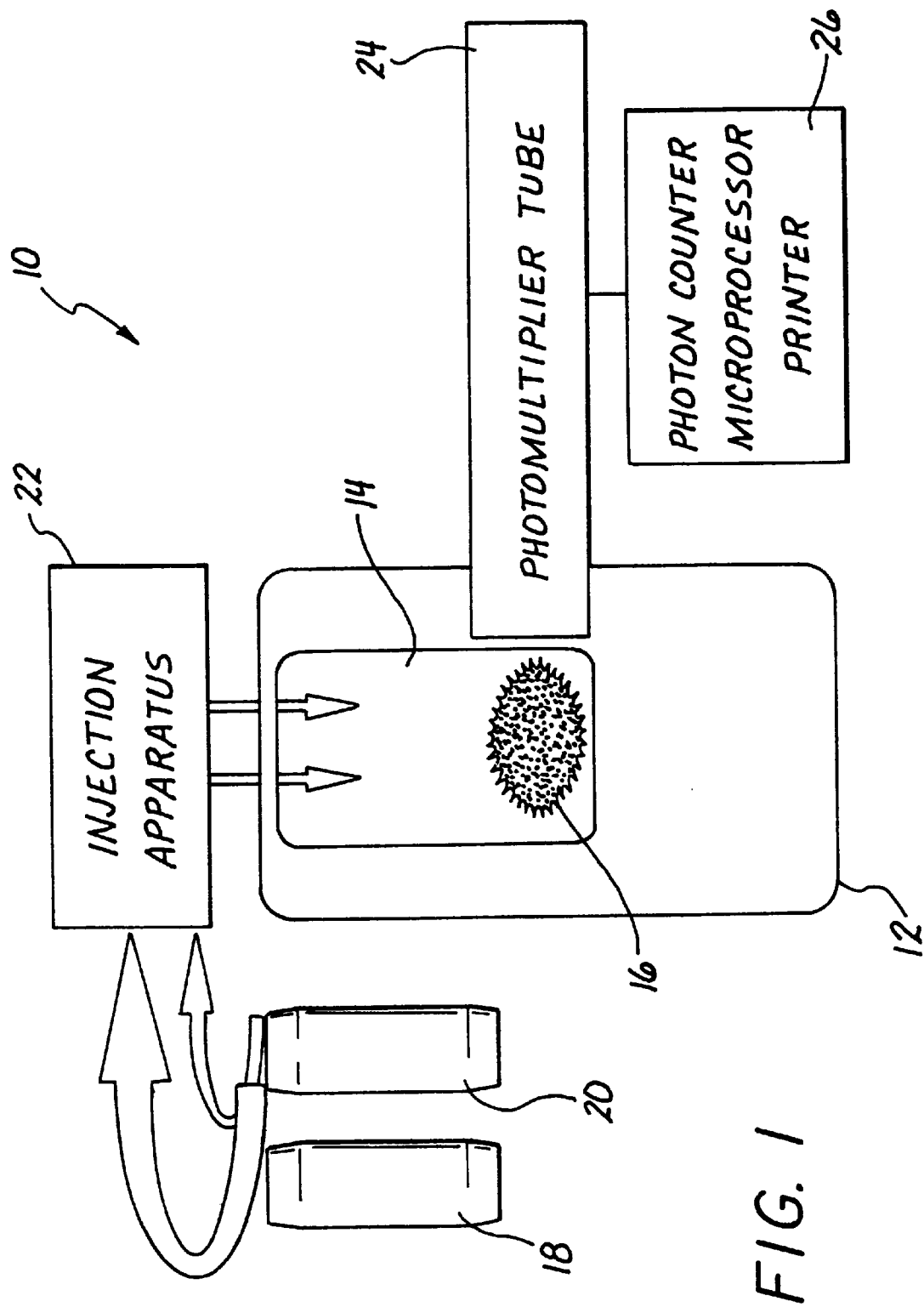
FIG. 1 is a schematic view illustrating an automated chemiluminescence immunoanalyzing system of the type usable with the present invention.

Referring now to FIG. 1, a schematic view of an automated chemiluminescence immunoanalyzer or luminometer 10 of the type utilized in the subject invention is illustrated. The luminometer 10 includes a housing 12 having a measuring chamber 14 therein, in which is disposed a sample cell 16, on which a tag or label has been incubated. In a preferred embodiment, the label may be an acridinium label, which may be intended, for example, for the quantitative determination of TSH concentrations in human serum, or alternatively, for the quantitative determination of Human Growth Hormone in human serum. In order to initiate the chemiluminescence reaction, a Trigger 1 reagent 18, which preferably comprises hydrogen peroxide in diluted acid, and a Trigger 2 reagent 20, which preferably comprises a strong base, such as diluted sodium hydroxide, are injected into the measuring chamber 14 by means of an injection apparatus 22, for oxidizing the acridinium ester. The oxidized product is in an excited state. The subsequent return to ground state results in the emission of light which is quantified in 2 seconds by a photomultiplier tube 24 and a photon counter 26, in known fashion, and is expressed in relative light units (RLU) by the system integrated luminometer 10.

Figure 2:
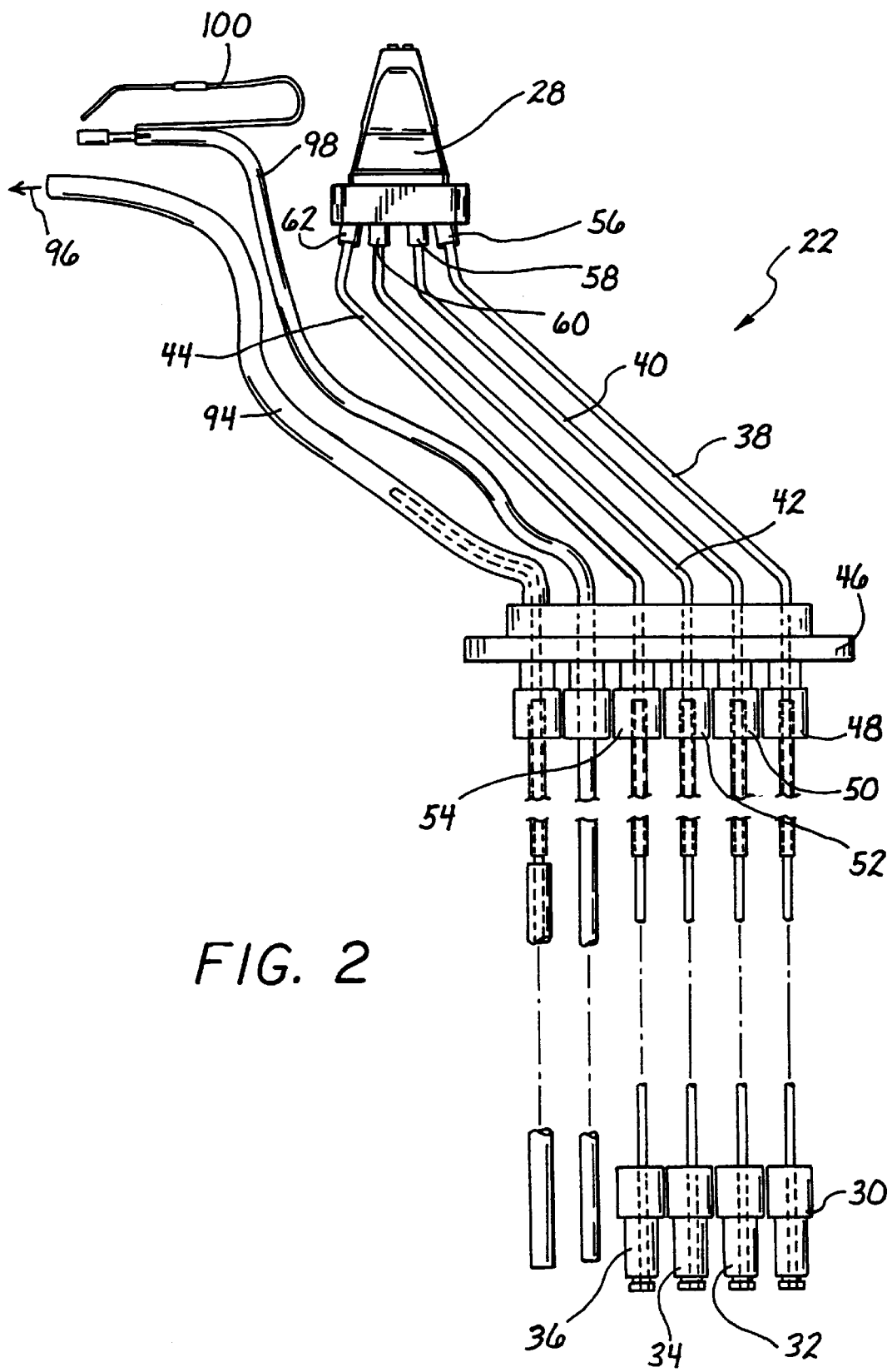
FIG. 2 is a top plan view, in isolation, of the trigger injection apparatus constructed in accordance with the principles of the present invention.
Figure 3:
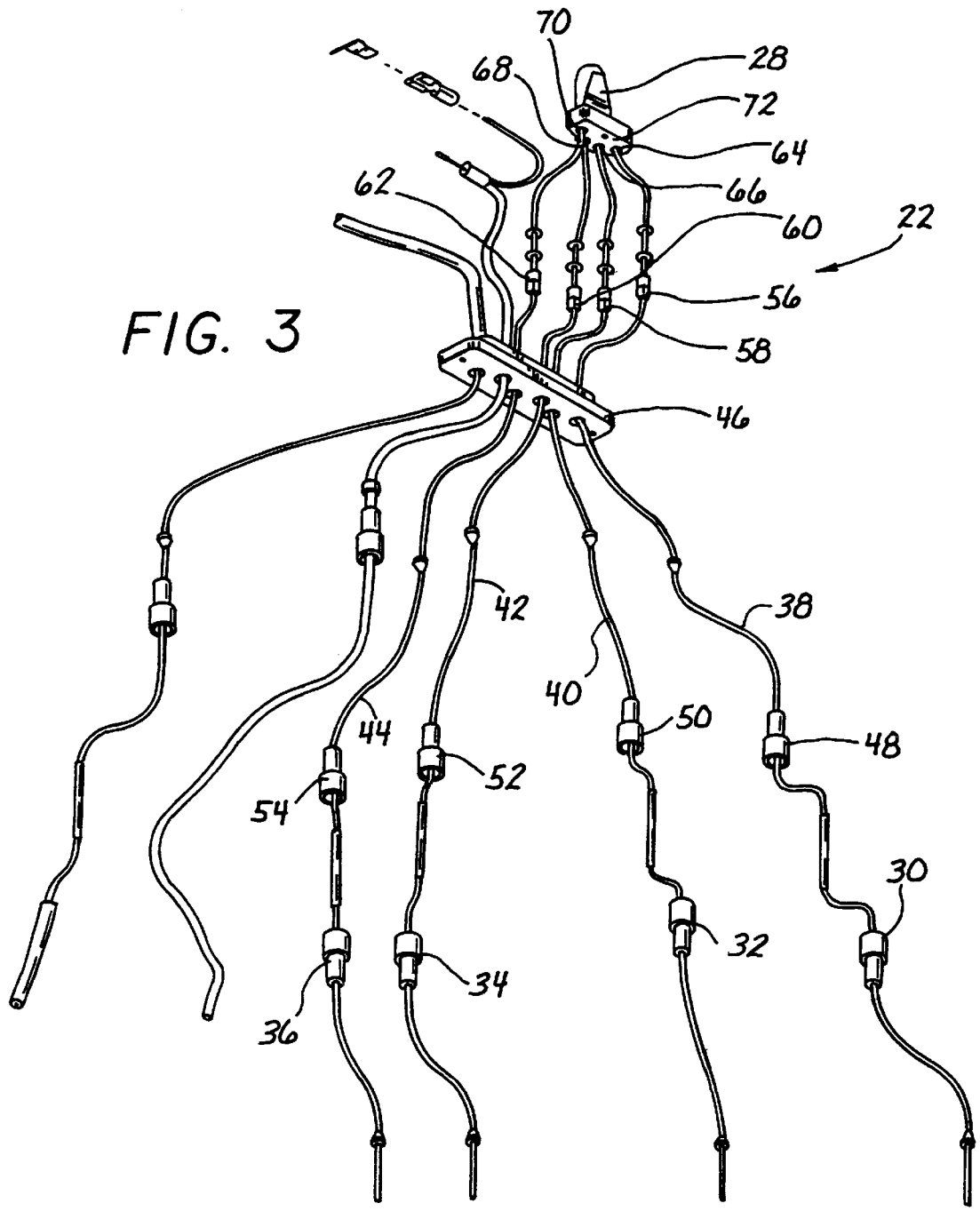
FIG. 3 is a perspective view of the trigger injection apparatus illustrated in FIG. 2.
Figure 10:
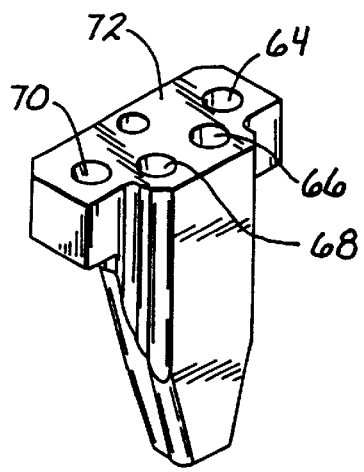
FIG. 10 is a perspective view, in isolation, illustrating the bottom side and proximal end of the trigger injector shown in FIG. 8.

With reference now to FIGS. 2, 3. and 8–18, the injection apparatus 22 of FIG. 1, modified in accordance with the principles of the invention to accommodate the injection of two different trigger reagent sets, will be described. The injection apparatus 22 includes an injector 28, which is preferably fabricated of an inert machined plastic, such as PEEK (polyetheretherketone), or, alternatively, of an inert material such as PTFE (TEFLON), which may be partially molded and thus less expensive to manufacture. Of course, other biocompatible materials and methods of manufacture may be used, if desired. Inlet fittings 30, 32, 34, and 36 are each adapted to receive a trigger reagent from a valve or pump connected to respective reagent reservoirs (not shown) for delivery to the injector 28 through fluid lines 38, 40, 42, and 44, respectively. Between the fittings 30, 32, 34, and 36, and the injector 28, is disposed a bulkhead plate 46, which is adapted for installing the tubing 38, 40, 42, and 44 to a bulkhead in the luminometer 10 in combination with fittings 48, 50, 52, and 54. In tun, the fluid lines 38, 40, 42, and 44 are connected to the injector 28 via threaded fittings 56, 58, 60, and 62, respectively. Each injection line is comprised of a single continuous liquid path to accomplish chemical inertness. The fittings 56, 58, 60, and 62 include o-rings, and are arranged to adjust and secure the tubes to the injector 28 by manipulating the threaded engagement between the fittings 56, 58, 60, and 62 and injector orifices 64, 66, 68, and 70 disposed on the proximal end 72 of the injector 28 (FIGS. 3, 9, and 10). These fittings function to prevent the tubing from moving relative to the injector 28 when the injector 28 moves up and down in the measuring chamber, as will be described hereinbelow. On the distal end 74 of the injector 28 are disposed four outlet orifices 76, 78, 80, and 82 (FIG. 8).

Figure 11:
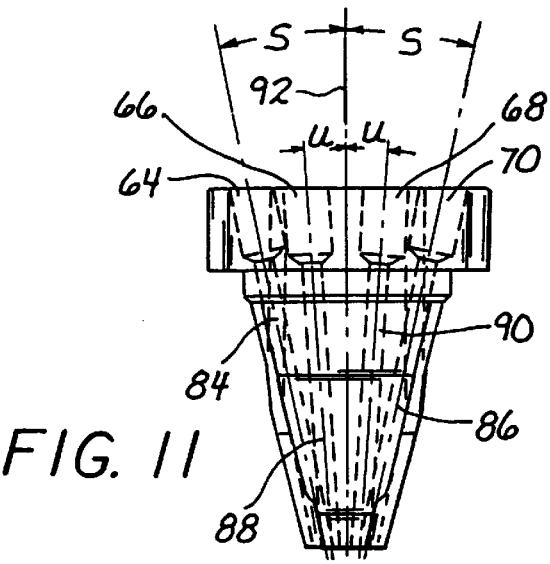
FIG. 11 is a plan view of the top side of the trigger injector shown in FIG. 8, illustrating in phantom each of the four trigger injection passages.
Figure 14:
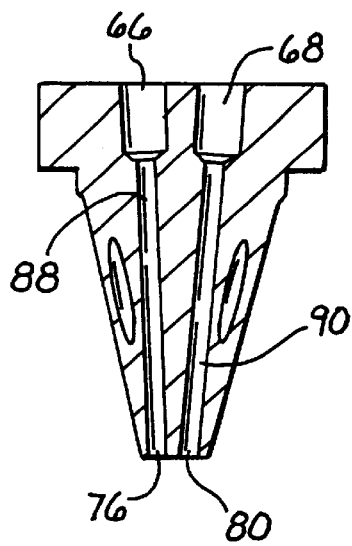
FIG. 14 is a cross-sectional view of the trigger injector shown in FIG. 8, taken along lines 14—14 of FIG. 12.
Figure 15:
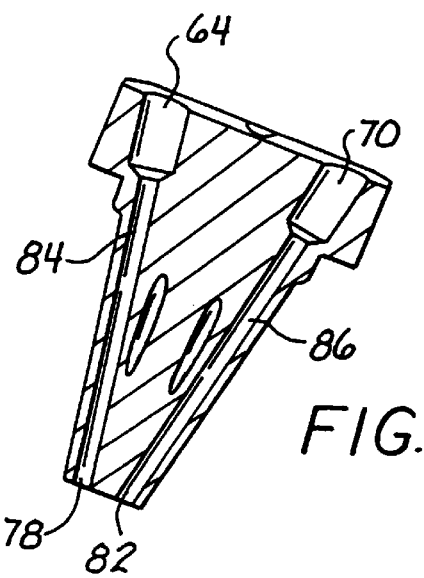
FIG. 15 is a cross-sectional view of the trigger injector shown in FIG. 8, taken along lines 15—15 of FIG. 12.
Figure 16:
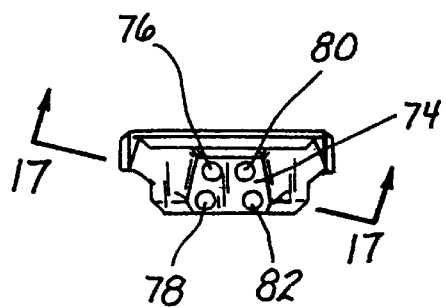
FIG. 16 is a plan view of the distal end of the trigger injector shown in FIG. 8.
Figure 17:
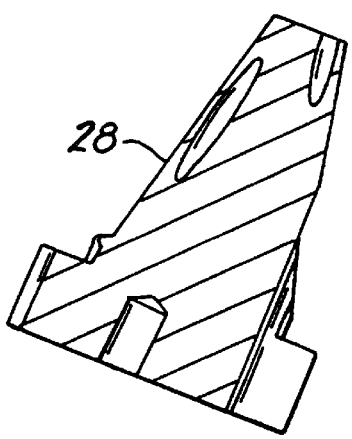
FIG. 17 is a cross-sectional view of the trigger injector shown in FIG. 8, taken along lines 17—17 of FIG. 16.
Figure 18:
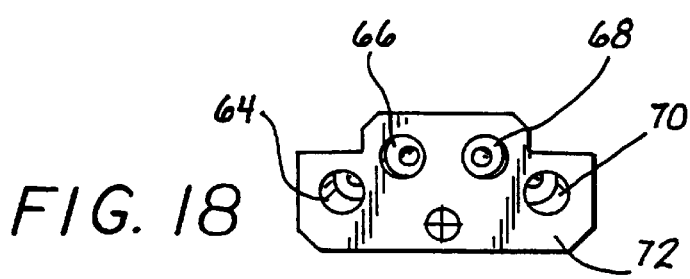
FIG. 18 is a plan view of the proximal end of the trigger injector shown in FIG. 8.

As is clear from FIGS. 11, 14, and 15, proximal orifice 64 of the injector 28 fluidly communicates with distal orifice 78 of the injector via passage 84, which is preferably machined (or molded) into the injector body 28. Similarly, orifices 70 and 82 communicate with one another through passage 86, orifice 66 communicates with orifice 76 through passage 88, and orifice 68 communicates with orifice 80 via passage 90.

Figure 12:
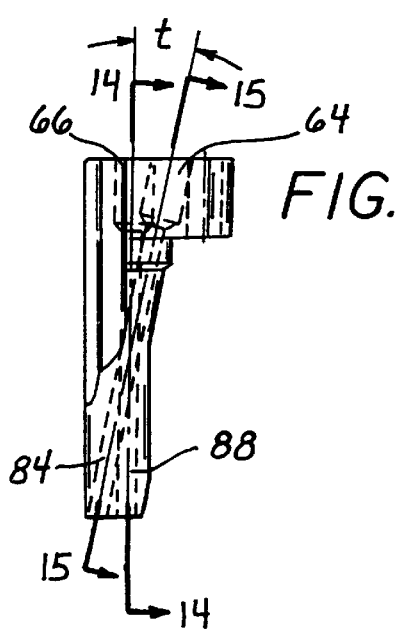
FIG. 12 is a plan view of the right side of the trigger injector shown in FIG. 8.
Figure 13:
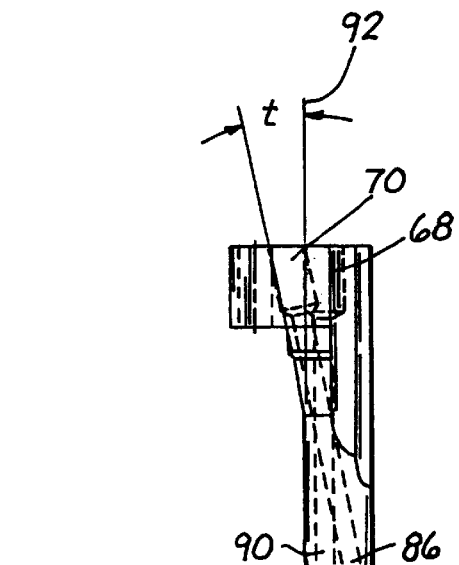
FIG. 13 is a plan view of the left side of the trigger injector shown in FIG. 8.

An advantageous feature of the present invention is that each of the outer orifices 64, 70, and their associated passages 84, 86, respectively, are disposed at a compound angle, meaning that they are disposed at an angle with respect to an axis 92 (FIGS. 11 and 13), which is the longitudinal axis of the injector 28, in two dimensions. More specifically, as can be seen from the aforementioned FIG. 11, the passages 84 and 86 are disposed at an angles with respect to the axis 92, or an angle 2s with respect to one another. Similarly, from FIGS. 12 and 13, it can be seen that the passages 84 and 86 are each disposed at an angle t from the axis 92 in a direction transverse to that of angle s. In other words, if the axis 92 were considered to be the x axis in a coordinate system, the angle s would be considered to lie in the y-plane, and the angle t would be considered to lie in the z-plane. The presently preferred value for angle s is within the range of 0–45 degrees, preferably 10–20 degrees, and preferably about 11 degrees, and the presently preferred value for angle t is also within the range of 0–45 degrees, preferably 10–20 degrees, and more preferably about 16–17 degrees.

The passages 88 and 90, on the other hand are preferably oriented substantially vertically, so that they are at an approximately 0 degree angle with respect to the axis 92 in the z-plane (FIGS. 12 and 13) and at an angle u with respect to the axis 92 in the y-plane, where the angle u is preferably within the range of 0–10 degrees, and more preferably about 3.6 degrees. As will be described more particularly hereinbelow, the passages 88 and 90 are adapted for injecting the second trigger reagent, for de-exciting the labels in order to produce detectable light, and these small angles have been found to assist in minimizing splashback of solution upon injection and to promote thorough mixing of the triggers with the solution. Of course, other approaches may be taken as well, with larger angles of injections to promote these two objectives, if desired.

Referring again particularly to FIG. 2, there is also provided a waste line 94, which communicates with an aspiration pump in the direction of arrow 96, and a sensing line 98, which has an aspiration needle 100 and an electrical connection for determining whether fluid is present in the cuvette after aspiration, in order to detect whether there is a clog in the line.

In operation, when an assay is to be performed, the instrument 10 is operational using software which permits substantially automatic function of the entire procedure. Initially, a System Wash reagent is used to wash the instrument's pipette probes. Afterwards, one or more assays are prepared, and labeled with a chemiluminescent tag, such as acridinium, or luminol, or both For example, a single patient's fluid specimen could be labeled with an acridinium ester for detection of an endocrinological condition, and simultaneously labeled with a luminol tag for detection of tumors. Alternatively, the system could be set up to analyze only a single assay, or to analyze two different assays in successive test specimens.

By way of example only, a TSH Third Generation assay could be analyzed. A TSH Third Generation assay is a two site chemiluminescence immunoassay for the measurement of TSH in human serum. It utilizes one mouse monoclonal antibody and a goat polyclonal antibody to TSH. The mouse monoclonal antibody is coupled to biotin, while the goat polyclonal antibody is labeled with an acridinium ester for detection. TSH is "sandwiched" between these antibodies. The sample containing TSH is incubated simultaneously with both antibodies. The formation of a soluble sandwich complex occur only in the presence of TSH molecules, which bridge the two antibodies. Therefore, only peptides that bridge these two antibodies can be quantitated.

Figure 5:
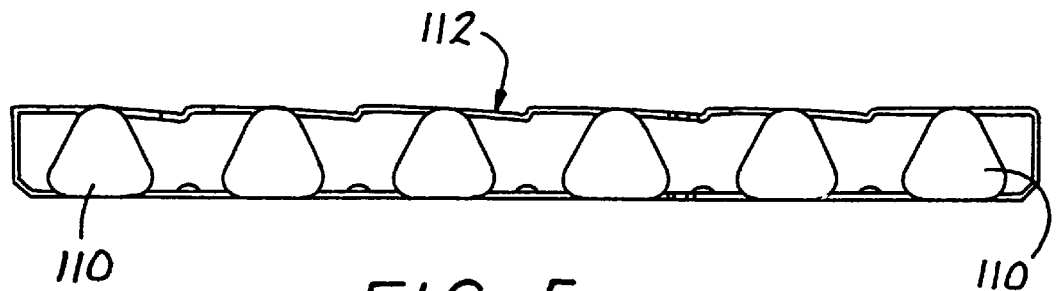
FIG. 5 is a bottom plan view of a cuvette strip for use in receiving the triggers injected by the trigger injector of the present invention.
Figure 6:
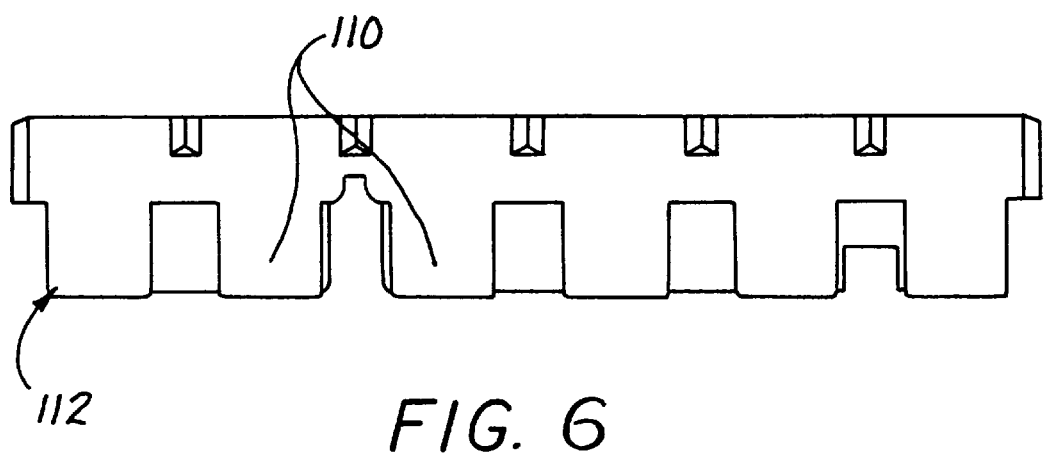
FIG. 6 is a side plan view of the cuvette strip illustrated in FIG. 5.
Figure 7:
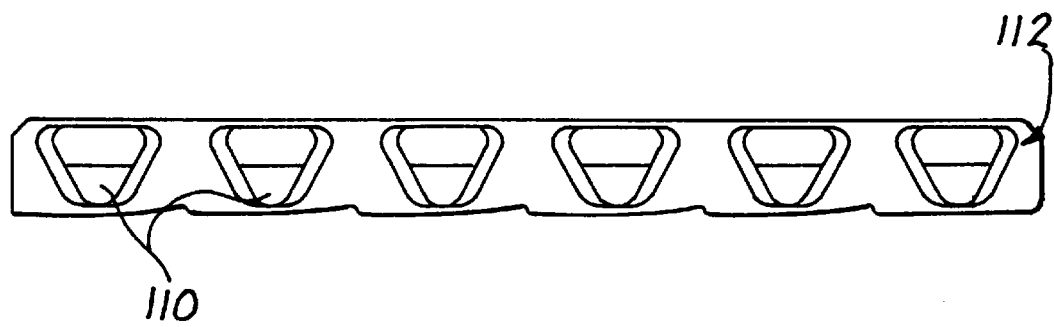
FIG. 7 is a top plan view of the cuvette strip illustrated in FIG. 5.

After an initial incubation period, streptavidin coated magnetic particles are added to the reaction mixture and a second incubation will follow. This allows for a highly specific and efficient means of binding the sandwich complex to the solid phase via the high affinity interaction between biotin and avidis. Free labeled antibody is separated from the labeled antibody bound to the magnetic particles by aspiration of the reaction mixture and subsequent washing using a concentrated assay wash reagent, as is known in the prior art. The sample reacted solutions are contained in wells 110 of a cuvette strip 112, illustrated in FIGS. 5–7, which is conveyed on a track through the instrument 10, first into the assay wash station (not shown) and then into the measurement chamber 14 (FIG. 1). The assay wash process functions to wash away the unreacted materials in order to reduce background levels for more precise results. Once the wells 110 of the cuvette 112 containing the washed magnetic particles are tansported into the measurement chamber 14, the injector 28, which is disposed in the mounting aperture 115 of a beam 117, is controlled using a stepper motor (not shown), so that the injector 28 descends vertically on the beam 117 to the top opening of one of the wells 110 of the cuvette 112, containing the assay. Once the injector 28 is in position, the Trigger 1 rent 18, preferably comprising Nitric acid, is injected into the cuvette well 110 from the orifice 78. Advantageously, because the orifice 78 is disposed at a compound angle with respect to the axis 92, the Trigger reagent strikes the walls of the well 110 at an angle and then flows downwardly into the sample fluid along the walls, thereby washing down the walls and resuspending the paramagnetic particles in the reacted complex solution.

Once the Trigger 1 reagent has been injected to resuspend the mixture, the Trigger 2 reagent 20, which preferably comprises sodium hydroxide, is injected from orifice 76 into the solution. As discussed supra, the orifice 76 is preferably disposed at a minimal angle with respect to the axis 92, because it is desirable to inject the Trigger 2 reagent straight into the solution with minimal splash back. While the Trigger 1 reagent functions to re-mix the solution and to excite the chemluminescent label, the Trigger 2 reagent functions to de-excite the label, thereby initiating the chemiluminescent flash for detection and quantification by the luminometer. The amount of bound labeled antibody is directly proportional to the concentration of TSH in the sample solution. Once quantified, the automated imnmunoanalyzer calculates test results for controls and patient samples from the observed signal from the calibration curve, and generates a printed report which includes patient information.

In the event that a second assay is to be analyzed, involving the use of different Trigger reagents; such as a Trigger 3 reagent and a Trigger 4 reagent, for a luninol label, for example, these reagents may be injected by a separate pump through the orifices 80 and 82, respectively, without the need to first stop the machine and clean the injection apparatus 22 (FIG. 1). This procedure is identical to the one discussed supra with respect to the Trigger 1 and Trigger 2 reagents, and it should be noted that the entire procedure could be reversed (i.e. the lumninol test could be performed first, followed by the acridinium test. Advantageously, because of the particular relative orientations of the four exit orifices 76, 78, 80, and 82, and the fact that the orifices 78 and 82 are oriented at a substantial compound angle with respect to the axis 92, the four orifices are adequately spaced on the distal end 74 of the injector 28 such that there is substantially no "cross-talk" between the four orifices. In other words, there is substantially no cross-contact between reagenlts exiting from each of the four orifices, and thus no contamination which might invalidate the assays.

While this invention has been described with respect to various specific examples and embodiments, it is to be understood that the invention is not limited thereto and that it can be variously practiced within the scope of the following claims.

What is claimed is:

1. A dual injector system for an automated chemiluminescent immunoassay instrument, comprising:

a first pair of injector orifices for injecting first and second trigger reagents into a well containing a chemiluminescent label; and a second pair of injector orifices for injecting third and fourth trigger reagents into said well containing a chemiluminescent label.

2. The dual injector system as recited in claim 1, and further comprising an injector having a lengthwise axis, wherein the first pair of injector orifices includes a first orifice for injecting the first trigger reagent into said well containing a chemiluminescent label and a second orifice for injecting the second trigger reagent into said well containing a chemiluminescent label.

3. The dual injector system as recited in claim 2, wherein the first orifice is disposed at an angle to said axis, such that the first trigger reagent injected therefrom washes down the walls of the well into which it is injected.

4. The dual injector system as recited in claim 3, wherein the first orifice is disposed at a compound angle to said axis, such that the first orifice is disposed at an angle to said axis in a plurality of planes.

5. The dual injector system is recited in claim 4, wherein said plurality of planes comprises two transverse planes.

6. The dual injector system as recited in claim 3, wherein said angle is between 0 and 45 degrees.

7. The dual injector system as recited in claim 3, wherein said angle is between 10 and 20 degrees.

8. The dual injector system as recited in claim 4, wherein said compound angle is between 0 and 45 degrees in each said plane.

9. The dual injector system as recited in claim 4, wherein said compound angle is between 10 and 20 degrees in a first plane, and between 10 and 20 degrees in a second plane.

10. The dual injector system is recited in claim 2, wherein the second orifice is disposed at an angle of less than 10 degrees from said axis in all planes.

11. The dual injector system as recited in claim 2, wherein the second pair of injector orifices includes a third orifice for injecting the third trigger reagent into said well containing a chemiluminescent label and a fourth orifice for injecting the fourth trigger reagent into said well containing a chemiluminescent label.

12. The dual injector system as recited in claim 11, wherein the third orifice is disposed at an angle to said axis, such that the third trigger reagent injected therefrom washes down the walls of the well into which it is injected.

13. The dual injector system as recited in claim 12, wherein the third orifice is disposed at a compound angle to said axis, such that the third orifice is disposed at an angle to said axis in a plurality of planes.

14. The dual injector system as recited in claim 13, wherein said plurality of planes comprises two transverse planes.

15. The dual injector system as recited in claim 12, wherein said angle is between 0 and 45 degrees.

16. The dual injector system as recited in claim 12, wherein said angle is between 10 and 20 degrees.

17. The dual injector system as recited in claim 13, wherein said compound angle is between 0 and 45 degrees in each said plane.

18. The dual injector system as recited in claim 13, wherein said compound angle is between 10 and 20 degrees in a first plane, and between 10 and 20 degrees in a second plane.

19. A dual injector system for an automated chemiluminescent immunoassay instrument, comprising:

an injector body having a longitudinal axis;

a first pair of injector orifices disposed on said injector body, for injecting first and second trigger reagents into a well containing a chemiluminescent label; and a second pair of injector orifices disposed on said injector body, for injecting third and fourth trigger reagents into said well or a second well containing a chemiluminescent label, wherein the third and fourth trigger reagents are different than the first and second trigger reagents.

20. The dual injector system as recited in claim 19, wherein the first and second trigger reagents function to excite and de-excite, respectively, a first type of chemiluminescent label, and the third and fourth trigger reagents function to excite and de-excite, respectively, a second type of chemiluminescent label.

21. The dual injector system as recited in claim 20, wherein the first type of chemiluminescent label comprises an acridinium ester and the second type of chemiluminescent label comprises a luminol.

22. The dual injector system as recited in claim 19, wherein said first and third orifices are each disposed at a compound angle to said axis.

* * * * *

UNITED STATES PATENT AND TRADEMARK OFFICE
CERTIFICATE OF CORRECTION

PATENT NO. : 6,056,923
DATED : May 2, 2000
INVENTOR(S) : Diamond et al.

It is certified that error appears in the above-identified patent and that said Letters Patent is hereby corrected as shown below:

Column 5,
Line 13, delete "angles" and insert -- angle s --.
Line 22, after "and" insert -- more --.
Line 56, after "both" insert -- . --.

Column 6,
Line 14, delete "avadis" and insert -- avadin --.
Line 32, delete "rent" and insert -- reagent --.

Signed and Sealed this

Second Day of April, 2002

Attest:

JAMES E. ROGAN
*Attesting Officer*  *Director of the United States Patent and Trademark Office*